United States Patent [19]
Chaumette et al.

[11] Patent Number: 5,776,988
[45] Date of Patent: Jul. 7, 1998

[54] PROCESS FOR CONVERTING SYNTHESIS GAS INTO HYDROCARBONS

[75] Inventors: Patrick Chaumette, Bougival; Pierre Boucot, Ternay; Frédéric Morel, Francheville, all of France

[73] Assignee: Institut Francais du Petrole, Rueil Malmaison, France

[21] Appl. No.: 745,288

[22] Filed: Nov. 8, 1996

[30] Foreign Application Priority Data

Nov. 10, 1995 [FR] France .................. 95 13338

[51] Int. Cl.⁶ .................................. C07C 27/06
[52] U.S. Cl. .................. 518/715; 518/713; 518/720; 502/307; 502/319
[58] Field of Search .................. 518/713, 715, 518/720; 502/307, 319

[56] References Cited

U.S. PATENT DOCUMENTS

| Re. 25,770 | 4/1965 | Johanson et al. | 208/10 |
|---|---|---|---|
| 4,312,741 | 1/1982 | Jacquin | 208/11 |
| 5,302,622 | 4/1994 | Chaumette et al. | 518/713 |

FOREIGN PATENT DOCUMENTS

| 2 490 668 | 3/1982 | France . |
|---|---|---|
| 897 549 | 11/1953 | Germany . |
| 770 8307 | 1/1979 | Netherlands . |

*Primary Examiner*—Gary Geist
*Assistant Examiner*—Sreeni Padmanabhan
*Attorney, Agent, or Firm*—Millen, White, Zelano, & Branigan, P.C.

[57] ABSTRACT

The invention relates to a process for synthesizing mainly linear and saturated hydrocarbons containing at least 80% by weight of $C_5+$ hydrocarbons in relation to all of the hydrocarbons formed, from a synthesis gas $CO-(CO_2)-H_2$, the synthesis gas being converted into hydrocarbons under a total pressure ranging between 0.1 and 15 MPa, the temperature ranging between 150° and 350° C., the hourly space velocity ranging between 100 and 30,000 volumes of synthesis gas per volume of catalyst and per hour, and the $H_2/CO$ molar ratio in the synthesis gas ranging between 1:2 and 5:1, said process being characterized in that it is carried out in a reaction zone with an ebullating catalytic bed in the presence of a catalyst comprising at least one metal from group VIII, and in the presence of a liquid phase.

20 Claims, 1 Drawing Sheet

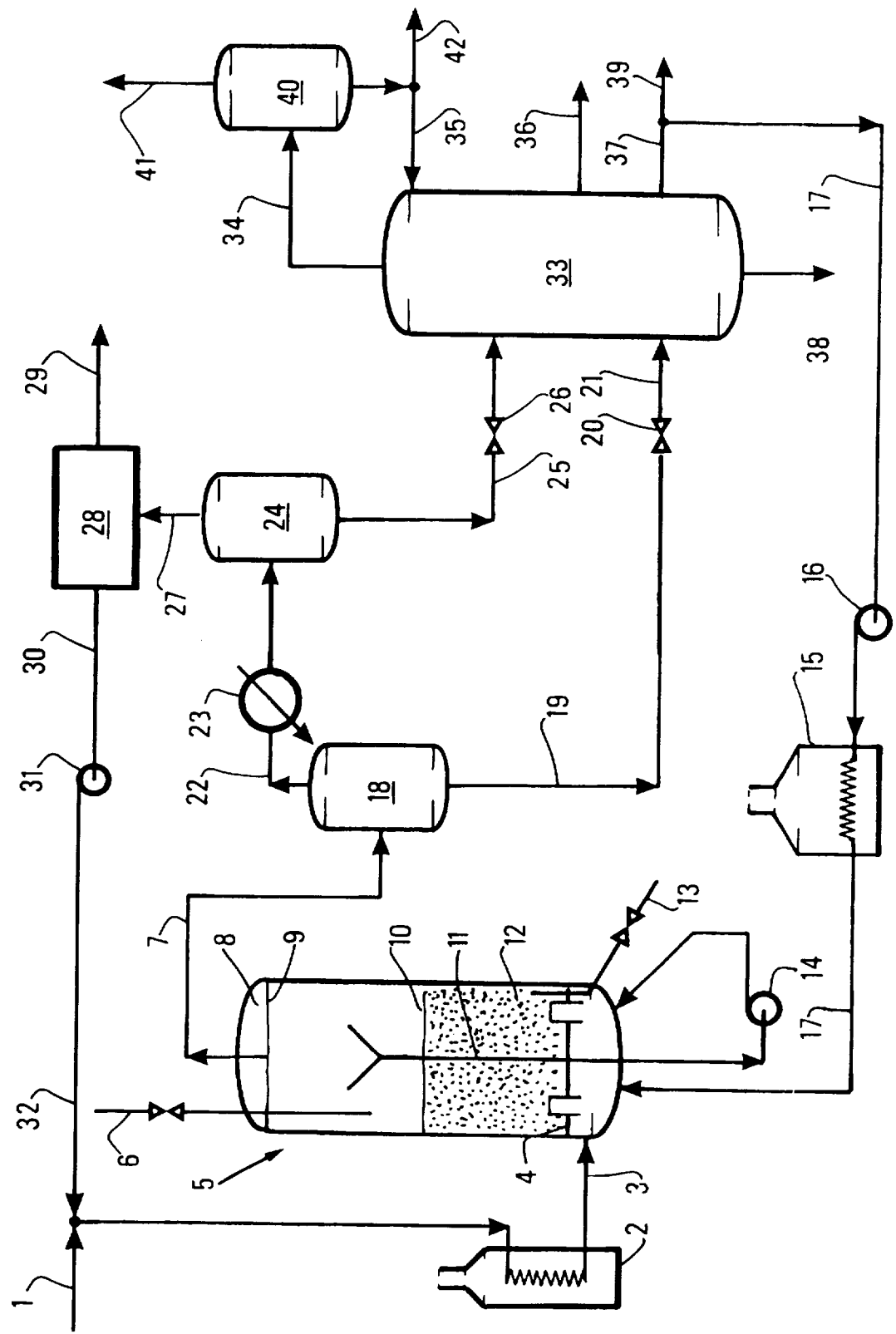

PROCESS FOR CONVERTING SYNTHESIS GAS INTO HYDROCARBONS

FIELD OF THE INVENTION

The present invention relates to a process for synthesizing hydrocarbons from a CO—($CO_2$)—$H_2$ mixture, i.e. a CO—$H_2$ mixture possibly comprising $CO_2$ called synthesis gas. More specifically, it relates to the use of a technology (ebullating catalytic bed also called three-phase fluidized bed) in the presence of a liquid phase and of a catalytic formulation allowing the synthesis gas to be converted into a mixture of linear and saturated hydrocarbons mainly consisting of $C_5$+ hydrocarbons (i.e. with at least 5 atoms of carbon per molecule), or more precisely into a mixture of mainly linear and saturated hydrocarbons, containing at least 80% by weight of $C_5$+ hydrocarbons in relation to all of the hydrocarbons formed, usable as gasoline or liquid fuel.

BACKGROUND OF THE INVENTION

It is well known to the man skilled in the art that synthesis gas can be converted into hydrocarbons in the presence of catalysts containing transition metals. This conversion, performed under heat and pressure, is referred to in the technical literature as the FISCHER-TROPSCH synthesis. Metals from the group VII of the periodic table of elements, such as iron, ruthenium, cobalt and nickel, thus catalyze the conversion of CO—($CO_2$)—$H_2$ mixtures into liquid and/or gaseous hydrocarbons.

Products prepared by FISCHER-TROPSCH synthesis in the presence of catalysts containing metals from group VIII exhibit a very wide distribution in terms of molecular weight. Only a small proportion of the products obtained thus is in the range of the middle distillates consisting of kerosine and gas oil fractions, the kerosine fraction(s) consisting of a mixture of hydrocarbons whose boiling points range between 140° and 300° C., and the gas oil fraction(s) consisting of a mixture of hydrocarbons whose boiling points range between 180° and 370° C. during an atmospheric distillation such as that performed by the man skilled in the art on a crude oil.

Considerable efforts have been started since 1973 to improve the middle distillate yield of processes based on the conversion of synthesis gas. In particular, cobalt-based catalysts have been used. The catalyst described in patent U.S. Pat. No. 5,302,622, comprising cobalt, copper and ruthenium, and prepared by gelation, allows to obtain a mixture of mainly linear and saturated hydrocarbons containing at least 80% by weight of $C_5$+ hydrocarbons in relation to all of the hydrocarbons formed. Similarly, the catalyst described in French patent FR-2.677.992 contains cobalt, at least one additional element M (for example in metallic form or in the form of an oxide) selected from the group consisting of molybdenum and tungsten and at least one additional element N (for example in metallic form or in the form of an oxide) selected from the group consisting of the elements of groups Ia, IIa, Ib (such as sodium, potassium, magnesium, calcium, copper or silver for example), ruthenium, palladium, uranium, praseodymium and neodymium, preferably from the group consisting of sodium, potassium, ruthenium, copper and uranium, all these elements being dispersed on a support consisting preferably of at least one oxide of at least one element selected from the group made up of the following elements : Si, Al, Ti, Zr, Sn, Zn, Mg, Ln (where Ln is a rare earth). Finally, French patent application 95/11.296 filed on Sep. 25, 1995 relates to a catalyst comprising a support including at least one oxide of an element Si, Al, Ti, Zr, Sn, Zn, Mg or Ln (where Ln is a rare earth), cobalt, at least one element A selected from the group consisting of ruthenium, platinum, palladium and uranium, at least one element B selected from the group consisting of molybdenum and tungsten. Its particular preparation comprises at least the successive stages as follows:

(1) forming a precursor comprising at least cobalt and at least part of the support (2) reducing at least partly said precursor in the presence of at least one reducing compound, and (3) depositing on the reduced precursor any compound part present in the catalyst and not present in the forerunner.

Furthermore, Fischer-Tropsch synthesis processes are processes that are generally carried out in the gas phase or in the liquid phase. The catalytic bed placed in the Fischer-Tropsch synthesis reactor is generally fixed, circulating, fluidized or expanded.

15 years ago, it had been considered using, for implementing the Fischer-Tropsch synthesis, a reactor in which the catalytic bed was run as an ebullating bed. In this way NL 7.708.307 and FR 2.490.668 mentioned in a general way the possible implementation of an ebullating bed. It has also been contemplated more precisely to run the catalyst bed as an ebullating bed, in the presence of an iron-based catalyst, treated with sulfur (U.S. Pat. No. 4,242,234 and U.S. Pat. No. 4,256,654) or chlorine (U.S. Pat. No. 4,172,842 and U.S. Pat. No. 4,252,685) and operated at a high temperature (at least 300° C.), so as to maximize the light hydrocarbon yield. In these implementations, the catalytic bed is expanded and fluidized by means of a sufficiently high gas flow. No liquid phase is fed or recycled into the reaction section apart from the reaction products. The calories produced by the reaction are eliminated by means of internal exchanges and of the gas phase.

SUMMARY OF THE INVENTION

The present invention relates to a process for synthesizing mainly linear and saturated hydrocarbons containing at least 80% by weight of $C_5$+ hydrocarbons in relation to all of the hydrocarbons formed, from a feed containing carbon monoxide CO, hydrogen $H_2$ and possibly carbon dioxide $CO_2$, called synthesis gas, said process being characterized in that it is performed in a reaction zone with an ebullating catalytic bed in the presence of a catalyst containing at least one metal from the group VIII of the periodic table of elements, preferably selected from the group consisting of iron and cobalt, more preferably cobalt, and in the presence of a liquid phase.

This process has the advantage of eliminating the heat produced by the reaction more efficiently and therefore of preventing too high a temperature increase at the level of the catalyst grain. Improved $C_5$+ hydrocarbon synthesis performances are obtained thereby.

The implementation conditions of the process according to the invention are usually the following.

The mixture is charged into the reaction zone with a $H_2$/CO molar ratio ranging between 1:2 and 5:1, preferably between 1.2:1 and 2.5:1. Said mixture can also contain carbon dioxide $CO_2$ and possibly other impurities such as hydrocarbons (methane, ethane, propane and butanes). The reaction temperature ranges between 150° and 350° C., preferably between 170° and 300° C. and more preferably between 180° and 280° C. The pressure ranges between 0.1 and 15 MPa, preferably between 1 and 10 MPa. The hourly space velocity ranges between 100 and 30,000, preferably between 400 and 10,000 volumes of synthesis gas per volume of catalyst and per hour. The liquid velocity, i.e. the velocity of the liquid phase in the presence of which the synthesis is carried out, ranges between 0.1 and 10 volumes of liquid per volume of catalyst and per hour, preferably between 0.2 and 5 volumes of liquid per volume of catalyst and per hour.

The liquid phase in the presence of which the process takes place is initially fed into the reaction zone in order to act as a heat carrier and to expand the catalytic bed. Then, once the reaction has started, at least part of the effluent of the reaction zone is preferably recycled to said zone within the scope of the present invention, possibly after fractionation, so as to obtain said liquid phase. The ratio of the volume of recycled liquid to the volume of feed generally ranges between about 0.5:1 and at least 50:1, preferably between 2:1 and 10:1.

Within the scope of the present invention, it is also possible to use at least one heat transfer means, generally in the form of an exchanger, so as to eliminate at least part of the heat produced by the reaction.

The catalyst used in the process according to the invention is a catalyst comprising at least one metal from group VIII, preferably selected from the group consisting of iron and cobalt, more preferably cobalt, known to the man skilled in the art for performing the Fischer-Tropsch synthesis. The catalysts whose formulation is described in patents U.S. Pat. No. 5,302,622 and FR-2,677,992 and in French patent application 95/11,296 for example can be more preferably used. The size of the catalyst is suited for use in an ebullating catalytic bed. When the mean equivalent diameter of the catalytic particles forming the catalyst ranges between 100 and 5000 μm (1 μm=1.10$^{-6}$ m=1 micron), preferably between 350 and 3000 μm, the surface velocity of the ascending liquid generally ranges between 0.5.10$^{-3}$ and 15 m/s, preferably between 0.1 and 10 m/s. In such a situation, the catalyst is periodically discharged spent from the reaction zone while fresh catalyst is added into said zone. However, it is also possible to use an operation, preferably in a single stage, with a catalyst added with the feed. In the reaction zone, which is generally a reactor, the density of the catalytic particles, the velocity of the ascending liquid and the ascending effect of the gases (mainly hydrogen and carbon monoxide) are important factors for the expansion and the use of the catalytic bed. By controlling the size and the density of the catalytic particles, and the velocities of the gases and of the liquids, while taking account of the viscosity of the liquid and of the operating conditions, the catalytic bed expands to a controlled height.

The Fischer-Tropsch synthesis reaction allowing the conversion of the synthesis gas (mixture of hydrogen and carbon oxide(s)) is highly exothermic. This is the reason why large amounts of heat have to be extracted from the reaction zone. The reaction zone, generally at least one reactor, the reactors being connected in series when the reaction zone includes at least two reactors, comprises a hot feed inlet and a grid supporting the catalyst, so that the liquid and the gas that are fed into the reactor, which run through the reactor in an ascending flow, expand the catalytic bed by at least 10% and up to 50% in relation to the height of said bed at rest, and place the catalyst in a random movement in the liquid. The feed and the recycled liquid are fed into the reaction zone at a velocity sufficient to provide a surface velocity ranging between 0.5.10$^{-3}$ and 5 m/s, preferably between 0.1 and 10 m/s, so that the bed is expanded and maintained under ebullating conditions by the liquid flow that flows up through the reactor. Such an ebullition of the catalytic bed produces an excellent heat transfer through the catalytic bed, preventing the formation of hot spots and helping towards the heat transfer from each point of the bed to the heat transfer means that is (are) possibly present in the reaction zone. For ebullating beds in which large heat transfers have to be performed, such means are typically steam generating tubes or coils, or any other means known to the man skilled in the art. The Fischer-Tropsch synthesis reaction is carried out in a liquid phase, generally containing hydrocarbons, comprising preferably at least 5, more preferably at least 10 atoms of carbon per molecule. A fraction of the effluent coming from the reaction zone is more preferably used.

The catalyst fed into the reaction zone is subjected to a prereduction prior to use, by at least one reducing compound selected for example from the group consisting of hydrogen, carbon monoxide and formic acid, possibly contacted with an inert gas (nitrogen for example) with a reducing compound/(reducing compound +inert gas) molar ratio ranging between 0.001:1 and 1:1.

The prereduction is carried out between 150° and 600° C., preferably between 200° and 500° C., between 0.1 and 10 MPa and at an hourly space velocity ranging between 100 and 40,000 volumes of mixture per volume of catalyst and per hour. This prereduction will preferably be conducted in the liquid phase comprising at least one hydrocarbon with at least 5, preferably 10 atoms of carbon per molecule.

The synthesis gas is thereafter converted into hydrocarbons according to the operating conditions described above The catalysts comprising at least one metal from group VIII, preferably selected from the group consisting of iron and cobalt, more preferably cobalt, used according to the invention, are particularly active and stable in the synthesis reaction of hydrocarbons from synthesis gas. Said catalyst allow to obtain mainly paraffinic hydrocarbons whose fraction exhibiting the highest boiling points can be converte( with a high yield into middle distillates (gas oil and kerosin( cuts) by means of a hydroconversion process such as cata lytic hydrocracking and/or hydroisomerization.

DESCRIPTION OF THE PREFERRED EMBODIMENTS

The FIGURE illustrates an embodiment of the proces according to the invention.

In the FIGURE, the compressed synthesis gas 1 (CC $CO_2$, $H_2$ mixture) is preheated by passing through a prehea furnace 2, at a variable temperature according to the tem perature at which the reaction is carried out. It is als possible to preheat the synthesis gas by means of a feed-tc effluent exchanger. The preheated synthesis gas 3 is fed int the ebullating bed reactor 5. A liquid hydrocarbor containing fraction 17 (gas oil cut) is also fed into reactor by means of a pump 16 with preheating in furnace 15.

Reactor 5 includes an inner distributor 4 that also acts a catalyst support. The liquid fed into the reactor thus allow to expand the catalytic bed 12 by about at least 10% an usually about 50% (catalyst level 10) above its height at re and to disperse the catalyst randomly in the liquid phas This reactor is described in patent U.S. Pat. No. Re. 25,77

According to the grain size of the catalyst, the latter is fe into the reactor either suspended in the liquid fractic (slurry), or through the specific feed 6. A part of the cataly can also be discharged through draw-off line 13.

The catalyst used is such as that described above.

It is generally necessary to recycle liquid situated above the catalyst level 10 towards the distribution plate 4 so as to generate a flow of liquid sufficient to keep the catalyst in motion in the liquid phase and to promote the reaction. The liquid is preferably recirculated by means of the central pipe 11 that extends below distribution plate 4 to the recycling pump 14. This procedure provides a controlled ascending flow of the liquid and through the catalytic bed 12. However, a recirculation by means of pipes exterior to the reactor and a combination of the two processes are also possible.

The space 8 in reactor 5 above the liquid level 9 is filled with the gas phase. A head fraction containing liquid and gas is drawn off by means of line 7 and fed into high-pressure separator 18. The gaseous fraction recovered mainly contains synthesis gas and light hydrocarbons. This fraction is fed into exchanger 23 through pipe 22 and then, after cooling, into the gas-to-liquid separator 24. The gaseous fraction obtained at the outlet of separator 24 is fed, by means of pipe 27, into a gas cleaning plant 28 generally comprising at least one cold box, possibly with purge 29.

After cleaning, the gas 30 obtained mainly contains synthesis gas and can be recompressed by means of compressor 31, then recycled through pipe 32 towards the synthesis gas feed of the reactor.

The liquid phase 19 recovered at the outlet of the high-pressure separator 18 is decompressed at 20, then fed into the atmospheric distillation column 33 through pipe 21. Similarly, the liquid fraction obtained at 25, after the gas-to-liquid separator 24, is decompressed at 26 and fed into atmospheric distillation column 33.

The gaseous fraction 34 coming from the atmospheric distillation column 33 is fed into a separator 40. This separation allows to obtain a low-pressure gas 41, as well as a liquid phase 35 acting as reflux in fractionating column 33, and to produce a naphtha cut 42.

The atmospheric distillation also allows to produce a kerosine cut at 36, as well as one or possibly several gas oil cuts at 37, and heavy paraffins at 38. Part of the gas oil cut obtained at 37 is recycled to reactor 5 via line 17, and another part is drawn off via pipe 39.

The following example illustrates the invention.

EXAMPLE

A catalyst based on cobalt, molybdenum and ruthenium deposited on silica is fed into the reactor shown in FIG. 1. This catalyst comprises 20% by weight of cobalt, 0.8% by weight of ruthenium and 0.2% by weight of copper. It has been prepared according to the protocol described in patent U.S. Pat. No. 5,302,622.

A liquid phase resulting from the Fischer-Tropsch synthesis, consisting of paraffinic hydrocarbons containing 15 to 40 atoms of carbon (light gas oil cut), is fed into the reactor and recycled.

This catalyst is reduced in the liquid phase at atmospheric pressure by a hydrogen-nitrogen mixture containing 6% by volume of hydrogen in nitrogen, then by pure hydrogen up to 350° C.

The liquid phase recycled into the reactor then results from the fractionation of the effluent coming from the synthesis reactor (see FIG. 1, gas oil cut).

Table 1 shows the performances obtained under these conditions.

TABLE 1

| Conversion of the synthesis gas into hydrocarbons | |
|---|---|
| Temperature (°C.) | 240 |
| Pressure (MPa) | 2 |
| $H_2/CO$ (moles) | 2 |
| $CO_2$ % (moles) | 3 |
| GHSV* (1/1 cata $h^{-1}$) | 700 |
| LHSV* (1/1 cata $h^{-1}$) | 0.32 |
| CO conversion (% by volume) | 80 |
| Hydrocarbons distribution (% by weight) | |
| Methane | 7.6 |
| $C_2$-$C_4$ hydrocarbons | 3.2 |
| $C_5^+$ hydrocarbons | 89.2 |

*Gas and liquid hourly space velocity

The liquid phase process according to the invention thus allows to limit the formation of methane and to reach a high selectivity and conversion to $C_5$+ hydrocarbons.

We claim:

1. A synthesis process for synthesizing mainly linear and saturated hydrocarbons containing at least 80% by weight of $C_5$+ hydrocarbons in relation to all of the hydrocarbons formed, from a feed comprising carbon monoxide CO, hydrogen $H_2$ and optionally carbon dioxide $CO_2$, said process being characterized in that it is carried out in a reaction zone with an ebullating catalytic bed in the presence of a catalyst comprising at least one metal from group VIII and in the presence of a liquid phase.

2. A process as claimed in claim 1, wherein the catalyst is subjected to a prereduction prior to use, said catalyst prereduction being performed by contacting with a mixture of inert gas and of at least one reducing compound with a reducing compound/(reducing compound+inert gas) molar ratio ranging between 0.001:1 and 1:1, the prereduction being conducted between 150° C. and 600° C., between 0.1 and 10 MPa at an hourly space velocity of 100 to 40,000 volumes of mixture per volume of catalyst and per hour.

3. A process as claimed in claim 1, wherein the conversion of the synthesis gas into hydrocarbons is performed under a total pressure ranging between 0.1 and 15 MPa, the temperature ranges between 150° and 350° C., the hourly space velocity ranges between 100 and 30,000 volumes of synthesis gas per volume of catalyst and per hour, the $H_2/CO$ molar ratio in the synthesis gas ranges between 1:2 and 5:1 and the liquid velocity ranges between 0.1 and 10 volumes of liquid per volume of catalyst and per hour.

4. A process as claimed in claim 1, wherein said liquid phase is a hydrocarbon-containing liquid phase.

5. A process as claimed in claim 1, wherein the liquid phase comprises at least one hydrocarbon with 5 atoms of carbon per molecule.

6. A process as claimed in claim 2, wherein the catalyst prereduction is performed in the presence of a liquid phase comprising at least one hydrocarbon with at least 5 atoms of carbon per molecule.

7. A process as claimed in claim 1, wherein the process produces an effluent and at least part of the effluent is recycled, after fractionation, into the reaction zone.

8. A process as claimed in claim 7, wherein the ratio of the volume of recycled liquid to the volume of feed ranges between 0.5:1 and 50:1.

9. A process as claimed in claim 1, wherein the catalyst is added to the feed.

10. A process as claimed in claim 1, wherein the catalyst is periodically discharged from the reaction zone while fresh catalyst is added into said zone.

11. A process as claimed in claim 1, wherein said metal from group VIII is selected from the group consisting of iron and cobalt.

12. A process as claimed in claim 1, wherein said metal from group VIII is cobalt.

13. A process as claimed in claim 2, the prereduction being conducted at between 200° and 500° C.

14. A process according to claim 1 further comprising removing an overhead stream from said reaction zone, subjecting said overhead stream to phase separation to recover a first liquid phase and a first gas phase, subjecting said first liquid phase to distillation to obtain several fractions; at least one of said fractions being a hydrocarbon containing at least 80% $C_5+$ hydrocarbons, and recycling at least part of said 80% $C_5+$ fraction into the reaction zone.

15. A process as claimed in claim 1, further comprising removing an overhead stream from said reaction zone, subjecting said overhead stream to phase separation to recover a first liquid phase and a first gas phase, cooling said first gas phase and subjecting the resultant cooled first gas phase to phase separation to recover a second liquid phase, and subjecting said second liquid phase to distillation to obtain several fractions, and recycling at least part of any hydrocarbon fraction containing at least 80% $C_5+$ hydrocarbons into the reaction zone.

16. A process as claimed in claim 14, further comprising removing an overhead stream from said reaction zone, subjecting said overhead stream to phase separation to recover a first liquid phase and a first gas phase, cooling said first gas phase and subjecting the resultant cooled first gas phase to phase separation to recover a second liquid phase, and subjecting said second liquid phase to distillation to obtain several fractions, and recycling at least part of any hydrocarbon fraction containing at least 80% $C_5+$ hydrocarbons into the reaction zone.

17. A process according to claim 16, wherein the first liquid phase and the second liquid phase are subjected to distillation in a single distillation column.

18. A process according to claim 1, wherein the liquid phase fed into the reactor is a paraffinic hydrocarbon containing 15 to 40 carbon atoms per molecule.

19. A process according to claim 7, wherein the liquid phase fed into the reactor is a paraffinic hydrocarbon containing 15 to 40 carbon atoms per molecule, and said recycled effluent comprises said paraffinic hydrocarbons.

20. A process according to claim 17, wherein the liquid phase fed into the reactor is a paraffinic hydrocarbon containing 15 to 40 carbon atoms per molecule.

* * * * *